(12) United States Patent
Kéri et al.

(10) Patent No.: US 6,706,192 B2
(45) Date of Patent: Mar. 16, 2004

(54) PURIFICATION PROCESS

(75) Inventors: Vilmos Kéri, Debrecen (HU); Árvai Nagyné, Debrecen (HU); Lajos Deák, Debrecen (HU); GyörgynéMakó, Debrecen (HU); IstvánnéMiskolczy, Debrecen (HU)

(73) Assignee: Biogal Gyogyszergyar Rt., Debrecen (HU)

( * ) Notice: Subject to any disclaimer, the term of this patent is extended or adjusted under 35 U.S.C. 154(b) by 91 days.

(21) Appl. No.: 10/144,841

(22) Filed: May 15, 2002

(65) Prior Publication Data

US 2002/0162789 A1 Nov. 7, 2002

Related U.S. Application Data

(63) Continuation of application No. 09/639,225, filed on Aug. 15, 2000, now Pat. No. 6,423,233, which is a continuation-in-part of application No. 09/194,494, filed as application No. PCT/HU98/00029 on Mar. 23, 1998, now abandoned.

(30) Foreign Application Priority Data

Mar. 25, 1997 (HU) ............................................. 9700645

(51) Int. Cl.[7] .............................................. B01D 15/08
(52) U.S. Cl. ................... 210/659; 210/198.2; 530/317; 530/321; 530/413; 530/417
(58) Field of Search ............................... 210/635, 656, 210/659, 198.2, 502.1; 530/317, 321, 413, 417

(56) References Cited

U.S. PATENT DOCUMENTS

| | | | | |
|---|---|---|---|---|
| 4,117,118 A | * | 9/1978 | Harri et al. ..................... 514/11 |
| 4,215,199 A | * | 7/1980 | Harri et al. ................. 435/71.1 |
| 5,382,655 A | * | 1/1995 | Szanya et al. ............... 530/317 |
| 5,439,591 A | * | 8/1995 | Pliura et al. ................. 210/635 |
| 5,545,328 A | * | 8/1996 | Pliura et al. ................. 210/635 |
| 5,605,623 A | * | 2/1997 | Afeyan et al. ........... 210/198.2 |
| 5,709,797 A | * | 1/1998 | Bocchiola et al. .......... 210/635 |
| 5,798,469 A | * | 8/1998 | Nufer ............................ 75/246 |
| 5,874,572 A | * | 2/1999 | Kim et al. ................... 540/460 |

FOREIGN PATENT DOCUMENTS

| | | | |
|---|---|---|---|
| CH | 589 716 | 7/1977 | ............... 210/198.2 |
| CH | 603 790 | 8/1978 | ............... 210/198.2 |
| CH | 630 062 | 5/1982 | ............... 210/198.2 |
| DE | 298276 | 3/1919 | ............... 210/198.2 |
| DE | 24 55 859 | 6/1975 | ............... 210/198.2 |
| EP | 029 122 | 10/1980 | ............... 210/198.2 |
| EP | 056 782 | 6/1982 | ............... 210/198.2 |
| HU | 201 577 | 7/1982 | ............... 210/198.2 |

OTHER PUBLICATIONS

Rüegger, A. et al., "Cyclosporin A, ein Immunsuppressiv Wirksamer Peptidmetabolit aus *Trichoderma Polysporum* (Link ex Pers.) Rifai", Helvetica Chimica Acta, vol. 59, No. 4, 1976, pp. 1075–1092.

Borel, J. F., et al., "Effects of the New Anti–Lymphocytic Peptide Cyclosporin A in Animals", Immunology: An Official Journal of the British Society for Immunology, vol. 32, 1977, pp. 1017–1025.

* cited by examiner

*Primary Examiner*—Ernest Q. Therkorn
(74) *Attorney, Agent, or Firm*—Kenyon & Kenyon

(57) ABSTRACT

Object of the invention is a process for the chromatographic purification of cyclosporin A from a crude product containing cyclosporin complex by using a column filled with silica gel and by the application of multistep chromatography with a column filled with normal phase silica gel and by a solvent mixture containing toluene as the major component.

21 Claims, No Drawings

PURIFICATION PROCESS

This application is a continuation of U.S. application Ser. No. 09/639,225, filed Aug. 15, 2000 now U.S. Pat. No. 6,423,233, which is a continuation-in-part of U.S. application Ser. No. 09/194,494, filed Apr. 1, 1999, now abandoned which, in turn, is a 371 of application No. PCT/HU98/00029, filed on Mar. 23, 1998.

The object of the invention is a process for the chromatographic purification of cyclosporin A from a crude product containing cyclosporin complex by using a normal phase—column filled with silica gel or an equivalent matrix and by the application of multistep chromatography with a column filled with normal phase silica gel or an equivalent matrix and by a solvent or solvent mixture containing toluene as the major component.

Cyclosporins are cyclic undecapeptides being N-methylated at several places and most of them having approved pharmacological effects. Twenty five members of this group of compounds have been known so far which are designated by letters A to Z. At first cyclosporin A was separated among them, which is a natural material and was isolated from the culture broth of Tolypocladium inflatum Gams strain (Helv. Chim. Acta 59 1075(1976)). This compound first became known as a slight antifungal antibiotic and later attracted the attention as an immunosuppressive. (J. F. Borel et al: Immunology 32 1017(1977)). Cyclosporin A is mainly used in organ transplantation from other persons (lung, heart, kidney, bone marrow, skin). Pharmacological examinations proved that it inhibits both the humoral and cellular immune responses by hindering the proliferation of T-cells and interrupting the synthesis of interleukin-2. Cyclosporin A also has been used for treating autoimmune and inflammatory diseases, such as in autoimmune hematological diseases, ulcerous colitis, Graves-illness, multiple sclerosis, psoriasis, rheumatic arthritis as well. Further experiments were done to cure infections caused by protozoa and tumors. The importance of cyclosporins is indicated by the fact, that number of synthetic related compounds call be prepared by building in different amino acids and substitutes. (e.g. EP 56782, CH 630062 and EP 29122 patents)

Cyclosporins are prepared by fermentation. Cylindrocarpon Lucidum Booth (patent specification No. CH 589,716); Trichoderma polysporum Rifai (patent specification No. CH 603,790); Tolypocladium varium (patent specification No. HU 201,577) are used to prepare cyclosporins. At the end of the fermentation, a cyclosporin complex is formed which may contain other impurities too (ingredients of culture media, anti-foaming agent, metabolites, etc.) depending on the character of the process.

Generally the product is isolated from the broth by extraction processes. This can be done by separating the mycelium from the broth by centrifugation or filtration, then dissolving the active ingredient from the mycelium by methanol or acetone and extracting the filtrate by water-immiscible solvents. An other known execution method is a process without filtration, using whole broth extraction with water-immiscible organic solvent. Solvent content of the organic phase is evaporated by vacuum distillation. However during the organic solvent extraction the compounds having lipid characters are also transferred into the organic phase, which cause difficulties in the further purification. In order to separate these compounds there are known processes (e.g. Swiss patent specification No. 589,716 or published German patent application No. 2455859) where after removing the extracting solvent the residue is dissolved in a mixture of methanol-water and then is extracted several times by the same volume of petroleum ether. Petroleum ether portions are combined and cyclosporins are recovered from them by a mixture of methanol-water. The active substance is transferred by multi-extraction from the combined methanol-water phase into ethylene chloride, which is then washed with water and evaporated to dryness. The crude product prepared by the above method and containing cyclosporins can be purified more efficiently by one of the chromatographic methods.

According to a method described in U.S. Pat. No. 4,117,118 the cyclosporin mixture is transferred first to a Sephadex LH-20 column and eluted with methanol, then it is eluted successively in an alumina column with a mixture of toluene and ethyl acetate (15%), and in a silica gel column with a mixture of chloroform and methanol (2%). Despite of the repeated chromatography the resulting product is not pure, but it is a mixture of cyclosporin A and B.

A similar chromatographic process is disclosed among others in the U.S. Pat. No. 4,215,199, where a rough-cleaning is with a 98:2% v/v mixture of chloroform and methanol on a silica gel column. The eluate is then evaporated to dryness. The residue is dissolved in methanol and is subjected to chromatography in a Sephadex LH-20 column using methanol as eluent. The eluate fractions are evaporated to dryness, then the residue is dissolved in 98:2% v/v mixture of chloroform and methanol. It is subjected again to a silica gel chromatography. Cyclosporin A appears first in the eluate. This and the consecutive fractions are separated, and the pure components are obtained by evaporating the elutes.

According to the German Pat. No. DD 298,276 the oily crude product is dissolved in small quantity of chloroform, then subjected to chromatography in an alumina column with chloroform. The fractions containing cyclosporin A are evaporated in vacuum, dissolved in chloroform, subjected to a similar column and then eluted by chloroform. Fractions containing the active substance are evaporated in vacuum again. Hexane is added to the residue and the cyclosporin A is crystallized. Product is washed by hexane then dried and finally recrystallized from a mixture of ether and hexane or acetone.

According to the Hungarian Pat. No. 201,577 the crude product obtained after evaporation can be cleaned on a silica gel column by elution with a mixture of chloroform and methanol gradually increasing concentration of methanol. The process is started by pure chloroform and continued by increasing in 0.5 vol % steps the methanol in the eluate. Cyclosporin A is eluted by 2 vol %, cyclosporin B by 2.5 vol %, cyclosporin C by 3 vol % methanol containing chloroform from the column. Components are obtained by evaporating the fractions.

Processes mentioned above describe mainly cyclosporin fermentation procedures, where the first aim of the purification steps is to identify the product obtained. Thus the product is isolated only in a small quantity and only the physical and chemical characteristics are given without publishing data relating to the purity of the product and the quantities of the impurities.

Rüieger and Co. /Helv.Chim. Acta 59(4), p. 1075–92 (1976) isolated small quantities of pure cyclosporin A and C by repeated chromatographies and by other purification steps for identification and structure analysis. According to this article the crude product received from the fermentation of Trichoderma polysporum Rifai containing mainly cyclosporins A and C is defatted with methanol and petroleum ether. After evaporation the residue is dissolved in chloroform and is subjected to chromatography by gradient elution with 98.5:1.5 v/v mixture of chloroform and methanol as eluent. Pure crystalline cyclosporin A is obtained by further chromatography. The fraction containing cyclosporin A is dissolved in methanol and is subjected to chromatography in a Sephadex LH-20 column by using methanol as eluent. Peak fractions are evaporated, dissolved in toluene and subjected to chromatography in a column packed with aluminum oxide, using toluene as eluent, in the presence of an increasing, concentration of acetic acid. The crystalline product is obtained after the evaporation of fractions and a treatment with activated carbon in all alcoholic solution.

A purification process feasible in industrial scale is described in the U.S. Pat. No. 5,382,655. According to the process the crude product containing different cyclosporin components is subjected to heat treatment prior to chromatography on silica gel column by the mixtures of chloroform-dichloromethane-ethanol or chloroform-ethyl acetate-ethanol. The product obtained is subjected to further chromatography and recrystallization, which resulted in a pure quality of product good for injection production.

Purification of the crude product containing the mixture of cyclosporins is very difficult, since the impurities having similar chemical structures are very similar in chromatographic characteristics to cyclosporin A as the main product. As the previously described processes prove, that regardless of the employed solvent mixture and because of the overlapping of the chromatographic peaks further chromatographic or other purification steps have to be carried out for obtaining certain components in pure form. The purification processes known so far are generally characterized by not only the fact, that their solvent requirement is considerable large, but the application of 3–4 different type of solvents or solvent mixtures and 2–3 types of column fillings are needed as well. As a consequence of these facts several type of chromatographic technics and regeneration methods are required within a process, which make difficulties in the development of a simple constructed and uniformly manageable economic industrial scale technology.

From environment protection point of view further problems are raised by the application of chlorinated hydrocarbons, since more and more countries have been making efforts for the limitation of their usage.

Regarding the filling materials of columns the application of aluminum oxide filling for industrial purposes is very doubtful, because as a consequence of its small specific surface the loading capacity and the separation ability is very small. Furthermore it is not advantageous for industrial purposes, because the aluminum oxide filling is rigid and easily fragile, thus it needs a special equipment and technology. Those can not be used in frequently emptied stainless steel columns generally used in the chemical industry.

Sephadex type fillings are very expensive ones, and in the case of the cyclosporin complex their efficiencies are very limited, since the sizes of molecules are very near to each others.

The object of the present invention is the development of an easily applicable chromatographic purification method in industrial scale which is suitable to manufacture the cyclosporin A ingredient containing much less impurities so far thus using it in medical practice in a safer way.

Our aim was to develop such a chromatographic purification technology, which requires only one type of solvent mixture and one type of column filling.

Because of its advantageous characteristics—high specific surface, high pore size, favorable sorption ability, easy handling and relatively low price—silica gel was used as a column filling. An ideal solvent mixture and a method had to be selected to this filling which is suitable to separate the cyclosporin components with high selectivity.

As a result of our experiments we recognized that our aim can be realized by multistep chromatography on silica gel column using a solvent mixture as an eluent which main component is toluene. Surprisingly it was found that even cyclosporin U and L components being the nearest to cyclosporin A can be separated by a three stages chromatography on silica gel column using toluene containing acetone as an eluent. These components differ from cyclosporin A only in a methyl group.

According to the first example of the application No. WO 94/16091 a solvent mixture of toluene and acetone is also used in a single stage. The product obtained is recrystallized from a solvent mixture of ether and hexane. (Yield: 66.6%.) The optical rotation of the product is sufficient, but its melting point is remarkably lower than that described in the literature, which indicates that the product is not pure. Thus, even recrystallization from a solvent will yield product of poor purity and a low yield.

Process according to the present invention is suitable to separate the most frequent impurities such as cyclosporins B and C being at present the largest quantities and moreover cyclosporin D, U and L components being at present in trace quantities. Cyclosporins B and C content of cyclosporin A end product obtained this way is less then 0.02 wt %, while cyclosporins L, U and D content is below 0.05 wt %.

The object of our invention is an improved process for the purification of cyclosporin A from a crude product containing cyclosporin complex which also enables the production of extremely pure cyclosporin A in large scales, with a chromatographic method on silica gel column using multistep chromatography with a solvent mixture containing toluene as the main component. Another new feature of the process is that we apply extremely high column load. In the conventional chromatographic practice the extent of column load amounts to not more than 5–10% of the column charge, and this value is lower for cyclosporins.

The crude product as used herein, refers to a product isolated from a fermentation broth by an extraction process. The crude product may contain, in addition to a cyclosporin complex, other organic or inorganic components. A cyclosporin complex, as used herein, is a complex which includes cyclosporin A and at least one other cyclosporin.

The chromatographic method of the procedure employs a stationary phase and a mobile phase. In the preferred mode, designated herein as multistep chromatography, the stationary phase consists of multiple normal phase columns. The normal phase column is typically a silica gel column or a material with equivalent properties. The mobile phases consists of a solvent or a solvent mixture which in the preferred mode contains toluene as the main component.

A new feature of the process is that we apply extremely high column load at least at the first purification step. Or preferably, we apply extremely high column load at least at one purification step. Column load refers to the cyclosporin A component of column charge, that is the mass of cyclosporin A loaded onto the first column relative to the mass of silica gel. In the conventional chromatographic practice the extent of column load amounts to not more than 5–10% of the column charge, and this value is lower for cyclosporins. In the present invention, the total mass of compounds applied to the first column is greater than about 20% of the mass of the silica gel absorbent. More preferably it is between, about 20 and 40% and most preferably between about 25 and 35%, of the mass of the silica gel absorbent. The extremely high column load of the present invention will accommodate a mass of cyclosporin A greater than about 0.100 kg, preferably between about 0.100 to 5.0 kg, more preferably between about 2–4.5 kg in the case of an 8 liter column. Higher column volumes causes a proportional mass of cyclosporin A. Thus, the larger the column volume, the larger the mass of cyclosporin A that may be purified by the methods of the present invention. For example, by the process of the present invention it is possible to purify even 10–20 kg samples of cyclosporin A using an extremely high column load and using a column that has an appropriate volume.

The multistep chromatography, the solvent mixture containing toluene as the main component and the high column load are interrelated and the desired result can only be achieved by their combined use. Therefore all three of above properties should be used simultaneously so as to obtain the extremely pure product.

According to the present invention preferably 2–4 chromatographic steps are applied subsequently and more expediently three steps.

The overload of the column is the highest in the first step of chromatography. The definite separation of the active substance and the impurities allows the use of high column load in the subsequent two steps of chromatography as well.

For the purification it is favorable to use a solvent mixture of toluene-acetone, which contains at most 30 vol % acetone.

According to all other favorable method a solvent mixture of toluene-ethyl acetate is used in which the ethyl acetate concentration is below 35 vol %.

In the purification process at least one time it is favorable to use gradient elution.

According to our experiments it was found that for the purification of the cyclosporin complex processed in our case is favorable to use 10–30 vol % and more favorable to use 13–18 vol % acetone and 10–35 vol % or 15–20 vol % ethyl acetate.

According to a possible method of the present invention the elution is done in the case of the three steps chromatography with toluene containing 15 vol % acetone or 18 vol % ethyl acetate. In the first step the major part of cyclosporin C is separated, in the second step the larger part of cyclosporin B, L and U components are removed, and finally in the third step the quantities of L and U components and other unidentified impurities can be reduced below 0.05 wt %. In the first step the cyclosporin A loss is minimal, however in the pre-fractions of the second and third steps a considerable quantity of cyclosporin A is removed together with the cyclosporin D component being very close to cyclosporin A. This cyclosporin A can be recovered in a very pure form in the fourth step.

For comparison in the table below the impurity profiles of cyclosporin A USP standard, the cyclosporin A active ingredient from SANDIMMUN® injection and also the data of the cyclosporin A product prepared by the present invention are given.

| Impurities | USP standard wt % | SANDIMMUN ® inj. wt % | Product according to the Example 1 wt % |
|---|---|---|---|
| Cyclosporin C | <0.02 | 0.17 | 0.05 |
| Cyclosporin B | <0.02 | 0.21 | 0.05 |
| Unknown | 0.09 | 0.35 | 0.05 |
| Cyclosporin L | 0.05 | 0.35 | 0.05 |

-continued

| Impurities | USP standard wt % | SANDIMMUN ® inj. wt % | Product according to the Example 1 wt % |
|---|---|---|---|
| Cyclosporin U | — | — | 0.05 |
| Cyclosporin D | 0.12 | — | 0.05 |

From the data it can be seen, that the quality of the cyclosporin A obtained by the present invention considerably exceeds the parameters of the SANDIMMUN® injection, as well as the USP requirements too.

Process according to the present invention is applicable for the purification of crude product both in small and large scales too.

Beside the fact that the process according to the present invention is able to prepare pure cyclosporin A, it has some not negligible advantages too. Since only one type of technological method (chromatography) is used, the purification process is manageable uniformly, moreover, it is repeatable and can be converted into a continuous process. Furthermore, there is a special advantage, that since only one type of solvent mixture is used in the three chromatographic steps, the regeneration of both the columns and the solvents became more simple.

A further special benefit of the process is that the first step of chromatography the highly binding impurities remain on the column, which greatly facilitates the regeneration of column charges in the subsequent two steps.

The present invention is introduced by the examples below without limiting the protection demand only to them.

In a comparative example (Example 4) it is presented, that with the application of a solvent mixture of dichloromethane-acetone in 3 steps chromatography generally used so far in the known process, could not be produced a final product in a similar purity.

EXAMPLE 1

Purification of Cyclosporin Crude Product with Three Steps Chromatography with the Application of a Solvent Mixture of Toluene-Acetone Quality of the starting cyclosporin crude product:

Cyclosporin A content 60.9 wt %

Cyclosporin B content 11.2 wt %

Cyclosporin C content 8.3 wt %

Cyclosporin L content 1.79 wt %

Cyclosporin U content 1.58 wt %

Cyclosporin D content 1.25 wt %

1st Step

Chromatography is done with two chromatographic columns connected in series, each one is 8 literss with jacket, diameter 10 cm, length 100 cm. Each of the two columns contains 3.95 kg Merck type Kieselgel silica gel with grain size 0.04–0.063 mm. In the First chromatography both columns contain fresh silica gel. In the case of the next chromatography the first column is separated and a second column is connected to it containing fresh silica gel. Further on for each chromatography only one new column is used. When the columns are changed and we use columns filled with fresh and used silica gel the column load is preferably between about 25% and about 80% calculated on the fresh silica gel.

Preparation of the Crude Product 4.1 kg with a purity of 60.9 wt % crude product is loaded to a pair of columns connected in series being dissolved previously in 15 liters toluene. 19 liter solution is received which is subjected to the top of the first column through a filter with a 2.4 l/h feeding rate. After loading the material is eluted with a solvent mixture of 13:87 vol % acetone-toluene until the volume of the effluent at the bottom of the second column is 39 liters. The cyclosporin content of the effluent is analyzed by TLC. Fractions not containing cyclosporin are collected as waste. 28 liter of the effluent after appearing the cyclosporin is considered as the main fraction. Dry material content of the intermediate I obtained this way is 3.23 kg.

Quality:
- cyclosporin A 75 wt %
- cyclosporin B 10. 1 wt %
- cyclosporin C 1.6 wt %
- cyclosporin L 1.7 wt %
- cyclosporin U 1.5 wt %
- cyclosporin D 1.3 wt %
- Yield calculated to cyclosporin A: 97%

$2^{nd}$ Step

Separation is done in a 1 meter length jacketed 8 liter Column. Column contains Merck Kieselgel 60 silica gel (0.015–0.040 mm). Mass of the filling is 3.95 kg. About 3 liter volume and 370 g dry material containing intermediate I solution obtained in the first step is subjected to the column with 2.4 l/h feeding rate, then it is washed with 1 liter toluene.

After loading the material the column is eluted with the mixtures of 10 liter 15:85 vol % acetone:toluene and then with 20 liter 25:75 vol % acetone:toluene solutions. The flow rate of the solvent till 17 liter fraction is 2.4 l/h, then from 18 liter fraction 5 l/h. Fractions are analyzed by TLC. 1–11 liter fractions are waste, fractions 12–19 liter are considered as critical 1 fractions and samples are taken from them. Impurity profiles of them are analyzed by FLPLC and those are handled as pre-fractions or combined with the main fractions. This way 80 g dry material containing pre-fraction can be received which is then evaporated to dryness.

20–25 liter fractions are combined as main fraction. 26–31 liter fractions are considered as critical fractions and after analysis those are combined with the main fraction or handled as post-fraction.

Main fraction obtained the above way is evaporated to dryness in a film evaporator mounted with an oscillating stirrer. 234 g of intermediate 11 is obtained with a yield of 80% and with a quality of the following:
- cyclosporin A 95 wt %
- cyclosporin U 1.2 wt %
- cyclosporin L 0.7 wt %
- cyclosporin B<0.1 wt %
- cyclosporin D 0.5 wt %
- cyclosporin C 0.1 wt %

$3^{rd}$ Step

Chromatography is done on the columns with the same construction and geometric sizes described in the 1st and 2nd steps.

A 1.7 liter toluene solution containing 220 g dry material is prepared from the intermediate 11 obtained in the second step and subjected to the top of the column with 2.4 l/h feeding rate, then it is washed with 1 liter toluene.

The column is eluted with a mixture of 20 liter 15:85 vol % acetone:toluene and then the cyclosporin is eluted with a mixture of 20 liter 25:75 vol % acetone:toluene.

The flow rate of the elution till 31 liter fraction is 2.4 l/h, then from 32 liter fraction 5 l/h.

1–18 liter fractions are waste, fractions 19–23 liter are pre-fractions and considered as critical I fractions. Samples are taken from them in order to analyze the dry material content and the impurity profiles by HPLC. After analysis those are handled as pre-fractions or combined with the main fractions. 29–38 liter fractions are combined as main fraction. 39–41 liter fractions are collected in 1 liter portions and considered as critical fractions 11. After analysis those are combined with the main fraction or handled as post-fraction.

As a result of the fractions collection after evaporation to dryness 70 g pre-fraction can be received.

Main fractions are combined and after evaporation to dryness 157 g pure cyclosporin is obtained with a yield of 75%. Quality of the product is the following:
- cyclosporin A 99.6 wt %
- cyclosporin L<0.05 wt %
- cyclosporin U<0.05 wt %
- cyclosporin D<0.05 wt %
- cyclosporin B<0.02 wt %
- cyclosporin C<0.02 wt %

EXAMPLE 2

Chromatographic Purification of Cyclosporin Crude Product on Stationary Bed Four Steps Silica Gel Column with the Application of Solvent Mixtures of Toluene-acetone or Toluene-ethyl Acetate Cyclosporin Crude product is purified with a three steps chromatography described in Example 1. Pre-fractions received in the three steps chromatography are purified in the fourth step in stationary bed with a solvent mixture of toluene-ethyl acetate.

$4^{th}$ Step

Construction and geometric sizes of chromatographic column is the same as described in Example 1. Column contains Merck Kieselgel 60 type silica gel (0.015–0.040 mm) as it is written in Example 1.

Column is subjected by a concentrate received from pre-fraction in the quantity of 260 g material dissolved in 2.5 liter toluene with a feeding rate of 2.4 l/h.
- cyclosporin A content 80.6 wt %
- cyclosporin D content 4.2 wt %

Subjected sample is washed with 1 liter toluene, then the column is eluted with a mixture of 20 liter 17:83 vol % ethyl acetate:toluene, by a flow rate of 2.4 l/h, then the elution is continued with a mixture of 40 liter 28:72 vol % ethyl acetate:toluene.

In the course of fractions collection the 1–19 liter fractions are waste. After HPLC analysis the 20–25 liter fractions are waste or combined with the main fraction. 26–35 liter fractions are collected as main fraction. After sampling and HPLC analysis the 36–42 liter fractions either combined with the main fraction or handed as waste. 23–42 liter collected main fraction described above is evaporated to dryness. This way 195 g pure cyclosporin A is obtained containing 99.6wt % active ingredient with a yield of 75% and with a quality of the following:
- cyclosporin A 99.6 wt %
- cyclosporin D<0.05 wt %
- cyclosporin U-
- cyclosporin L-

EXAMPLE 3

Chromatographic Purification of Cyclosporin Crude Product on Stationary Bed Two Steps Silica Gel Column with the Application of a Solvent Mixture of Toluene-acetone Cyclosporin crude product is purified according to the same process described in the 1st step of Example 1 obtaining cyclosporin intermediate I with the same quality. Further on the process is the following:

$2^{nd}$ Step

Column is subjected by 3 liter intermediate 1 containing 370 g dried material with a feeding rate of 2.4 l/h, then the subjected sample is washed with 1 liter toluene.

After loading the column is eluted with a mixture of 10 liter 15:85 vol % acetone:toluene, then the elution is continued with a mixture of 20 liter 25:75 vol % acetone:toluene.

The flow rate of the solvent is 2.4 l/h till 17 liter and 5 l/h from 18 liter.

According to TLC and HPLC detection 1–11 liter fractions are waste, 12–20 fractions are pre-fractions, 21–24 fractions are considered as the main fractions and fractions from 25 till the end are handled as post-fractions. Washing acetone fractions are waste.

After fractionation, the collected main fractions are combined and evaporated to dryness obtaining 114 g cyclosporin A with a yield of 41% and with as good quality of product as is written in Example 1.

EXAMPLE 4

Comparative Example for the Purification of Crude Product with 3 Steps Chromatography with the Application of a Solvent Mixture of Dichloromethane-acetone Quality of the starting cyclosporin crude product (the same as used in Example 1):

Cyclosporin A content 60.9 wt %
Cyclosporin B content 11.2 wt %
Cyclosporin C content 8.3 wt %
Cyclosporin L content 1.79 wt %
Cyclosporin U content 58 wt %
Cyclosporin D content 1.25 wt %

$1^{st}$ Step

Chromatographic equipment and the filling is the same as described in Example 1. One pair of column connected in series is subjected with 4.1 kg crude product with the purity of 60.9% in 15 liter dichloromethane solution.

After loading the sample the column is eluted with dichloromethane with a flow rate of 2.4 l/h till collecting 35 liter of effluent.

1–10 liter fractions are waste, while 11–35 liter fractions are considered as main fractions. Dried material content of intermediate 1 obtained this way is 2.9 kg, active ingredient content is 75 wt %.

$2^{nd}$ Step

Chromatographic equipment and the filling is the same as described in Example 1.

Column is subjected at the top by 3 liter intermediate 1 containing 350 g dried material with a feeding rate of 2.4 L/h. Elution is done with a mixture of 10 liters acetone:dichloromethane 1:9 vol. rate, then continued with a mixture of 25 liter acetone:dichloromethane 2:8 vol. rate and finished with acetone 2.4 l/h rate.

According to TLC analysis the volume of the pre-fraction was 13 liters, the volume of the main fraction was 22 liter, and the volume of the post-fraction was 11 liter. 22 liter of main fraction was evaporated to dryness and as a consequence 220 g intermediate 11 product was obtained with the purity of 91%.

$3^{rd}$ Step

Chromatographic equipment and the filling is the same as described in Example 1.

Filling is loaded by 220 g intermediate 11 feeding the dichloromethane concentrate with a rate of 2.4 l/h on the column. Elution is done with a mixture of 20 liters acetone:dichloromethane 1:9 vol. rate, then continued with a mixture of 30 liter acetone: dichloromethane 2:8 vol. rate and finished with acetone 2.4 l/h rate.

First 26 liter fractions are considered as pre-fractions, then 26 liter main fraction is collected and finally 11 liter post-fractions are taken. 26 liter of main fraction was evaporated to dryness and as a consequence 140 g intermediate III product was obtained with the following quality:

Cyclosporin A 98.6 wt %
Cyclosporin U 0.6 wt %
Cyclosporin D 0.3 wt %
Cyclosporin L 0.2 wt %
Cyclosporin B 0.1 wt %
Cyclosporin C 0.1 wt %

Although certain presently preferred embodiments of the invention have been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rules of law.

What is claimed is:

1. A process for purifying cyclosporin A comprising:
    a first step comprising
        loading a mixture including cyclosporin A onto a first silica gel column;
        eluting the first column with a first eluent comprising more than 50 vol % tolune to produce a first eluate containing purified cyclosporin A;
    a second step comprising
        loading the first eluate onto a second silicia gel column;
        eluting the second column with a second eluent comprising more than 50 vol % toluene to produce a second eluate containing cyclosporin A having a purity of about 95 wt % or greater.

2. The process of claim 1, further comprising:
    a third step comprising
        loading the second eluate onto a third silica gel column;
        eluting the third column with a third eluent comprising more than 50 vol % toluene to produce a third eluate containing cyclosporin A having a purity of about 99 wt % or greater.

3. The process of claim 2, further comprising:
    a fourth step comprising
        collecting non-peak eluate from the second and third steps;
        loading the non-peak eluate on a fourth silica gel column;
        eluting the fourth column with a fourth eluent containing cyclosporin A having a purity of about 99 wt % or greater.

4. The process of claim 3, wherein the fourth eluent in the fourth step further comprises ethyl acetate.

5. The process of claim 4, wherein the eluting step comprises employing a plurality of eluents within the range of about 10 to about 35 vol % ethyl acetate.

6. The process of claim 5, wherein the plurality of eluents comprises an eluent containing about 17 vol % ethyl acetate and another eluent containing about 28 vol % ethyl acetate.

7. The process of claim 2, wherein
a first silica gel column contains silica gel having grain size of about 0.04 mm or greater; and
the second silica gel column contains silica gel having grain size of about 0.04 mm or less.

8. The process of claim 2, wherein the process for purifying cyclosporin A consists essentially of three chromatographic steps.

9. The process of claim 1, wherein the mixture is heated to 80–120° C. prior to loading.

10. The process of claim 1, wherein the process for purifying is performed on an industrial scale.

11. The process of claim 1, wherein the column load of cyclosporin A on at least one column is about 20 wt %, or greater, of the mass of the silica gel absorbent.

12. The process of claim 1, wherein the column load of cyclosporin A in at least one chromatographic step is greater than 25 wt % to about 35 wt % of the mass of the silica gel absorbent.

13. The process of claim 1, wherein each eluent further comprises acetone.

14. The process of claim 13, wherein each eluent comprises from about 10 to about 30 vol % acetone.

15. The process of claim 14, wherein each eluting step comprises employing a plurality of eluents with the range of about 10 to about 30 vol % acetone.

16. The process of claim 15, wherein the plurality of eluents comprises an eluent containing about 15 vol % acetone and another eluent containing about 25 vol % acetone.

17. The process of claim 1, wherein the purity of the second eluate is about 99.6 wt % or greater.

18. The process of claim 1, wherein the column load of cyclosporin A in at least one step ranges from about 25 wt % to about 35 wt % of the mass of the silica gel absorbent.

19. A process for purifying cyclosporin A comprising:
a first step comprising
loading a mixture including cyclosporin A onto a first silica gel column;
eluting the first column with a first eluent comprising more than 50 vol % toluene to produce a first eluate containing purified cyclosporin A;
a second step comprising
loading the first eluate onto a second silica gel column;
eluting the second column with a second eluent comprising more than 50 vol % toluene to produce a second elute containing cyclosporin A having a purity of about 99 wt % or greater,
wherein the column load of cyclosporin A in at least one step ranges from about 25 wt % to about 35 wt % of the mass of the silica gel absorbent.

20. The process of claim 19, wherein the mixture is heated to 80–120° C. prior to loading.

21. A process for purifying cyclosporin A comprising:
a first step comprising
loading a mixture of cyclosporin A onto a first silica gel column;
eluting the first column with a first eluent comprising about 13:87 vol % acetone:toluene to produce a first eluate containing purified cyclosporin A;
a second step comprising
loading the first eluate onto a second silica gel column;
eluting the second column with a second eluent comprising an eluent containing about 15:85 vol % acetone:toluene and another eluent comprising about 25:75 vol % acetone:toluene to produce a second eluate containing purified cyclosporin A; and
a third step comprising
loading the second eluate on a third silica gel column;
eluting the third column with a third eluent comprising an eluent comprising about 15:85 vol % acetone:toluene and another eluent containing about 25:75 vol % acetone:toluene to produce a third eluate containing cyclosporin A having a purity of about 99 wt % or greater;
wherein the column load of cyclosporin A in at least one step ranges from about 25 wt % to about 35 wt % of the mass of the silica gel absorbent.

* * * * *

UNITED STATES PATENT AND TRADEMARK OFFICE
CERTIFICATE OF CORRECTION

| | | |
|---|---|---|
| PATENT NO. | : 6,706,192 B2 | Page 1 of 1 |
| APPLICATION NO. | : 10/144841 | |
| DATED | : March 16, 2004 | |
| INVENTOR(S) | : Vilmos Kéri et al. | |

It is certified that error appears in the above-identified patent and that said Letters Patent is hereby corrected as shown below:

Column 1, line 39, change "call be prepared" to --can be prepared--

Column 3, line 31, change "considerable" to --considerably--

Column 4, line 1, change "selected to this" to --selected for this--

Column 6, line 59, change "First" to --first--

Column 8, line 40, change "is" to --are--

Column 10, line 63, change "fourth eluent containing" to --fourth eluent comprising more than 50 vol % toluene to produce a fourth eluate containing--

Signed and Sealed this

Eleventh Day of March, 2008

JON W. DUDAS
*Director of the United States Patent and Trademark Office*